US005599417A

United States Patent [19]
Glaug et al.

[11] Patent Number: 5,599,417
[45] Date of Patent: Feb. 4, 1997

[54] METHOD OF MANUFACTURE OF LIQUID RETAINING ABSORBENT GARMENT

[75] Inventors: Frank S. Glaug, Appleton; David A. Kuen, Neenah; Robert L. Popp, Hortonville, all of Wis.

[73] Assignee: Kimberly-Clark Corporation, Neenah, Wis.

[21] Appl. No.: 440,039

[22] Filed: May 12, 1995

Related U.S. Application Data

[62] Division of Ser. No. 171,578, Dec. 22, 1993, Pat. No. 5,476,458.

[51] Int. Cl.$^6$ .............................. A61F 13/15; A61F 13/20
[52] U.S. Cl. .......................... 156/227; 156/164; 156/196; 156/297; 604/358
[58] Field of Search ...................................... 156/163, 164, 156/196, 200, 204, 227, 297; 604/358, 369, 373, 378, 385.1, 385.2, 393, 394, 396, 401, 402

[56] References Cited

U.S. PATENT DOCUMENTS

| Re. 33,106 | 11/1989 | Beckestrom . |
|---|---|---|
| 1,508,740 | 9/1924 | Brand . |
| 1,977,604 | 10/1934 | Alsop . |
| 2,004,088 | 6/1935 | Alsop . |
| 2,026,158 | 12/1935 | Bennett . |

(List continued on next page.)

FOREIGN PATENT DOCUMENTS

| 86044/82 | 1/1983 | Australia . |
|---|---|---|
| 21332/83 | 5/1984 | Australia . |
| 1211902 | 9/1986 | Canada . |
| 1216702 | 1/1987 | Canada . |
| 1302654 | 6/1992 | Canada . |
| 0190881A2 | 8/1986 | European Pat. Off. . |
| 0243013A1 | 10/1987 | European Pat. Off. . |
| 0251332A2 | 1/1988 | European Pat. Off. . |
| 0264952A2 | 4/1988 | European Pat. Off. . |
| 0268858A2 | 6/1988 | European Pat. Off. . |
| 0539703A1 | 5/1993 | European Pat. Off. . |
| 0549988A1 | 7/1993 | European Pat. Off. . |
| 2425205 | 12/1979 | France . |
| 63-21901 | 1/1988 | Japan . |
| 63-12705 | 1/1988 | Japan . |
| 63-230164 | 9/1988 | Japan . |
| 64-26310 | 2/1989 | Japan . |
| 64-77607 | 3/1989 | Japan . |
| 265859 | 3/1990 | Japan . |
| 380858 | 4/1991 | Japan . |
| 3198851 | 8/1991 | Japan . |
| 5184622 | 7/1993 | Japan . |
| 2188532 | 10/1987 | United Kingdom . |
| 2241871 | 9/1991 | United Kingdom . |
| 2266225 | 10/1993 | United Kingdom . |
| 2270247 | 1/1994 | United Kingdom . |
| 2268389 | 1/1994 | United Kingdom . |
| 9207536 | 5/1992 | WIPO . |
| WO93/09742 | 5/1993 | WIPO . |
| WO93/17648 | 9/1993 | WIPO . |
| WO94/03136 | 2/1994 | WIPO . |
| WO9410952 | 5/1994 | WIPO . |
| WO9410951 | 5/1994 | WIPO . |

*Primary Examiner*—John G. Weiss
*Assistant Examiner*—P. Zuttarelli
*Attorney, Agent, or Firm*—Thomas M. Gage

[57] ABSTRACT

An absorbent garment method of manufacture includes supplying a three-dimensional pant body defining a waist opening, two leg openings, and a crotch region. A containment trough formed of liquid impermeable material has a base portion bonded to the crotch region and integral retaining walls positioned transversely outward from the base portion. The retaining walls are freestanding from the pant body and include elastic members so as to define freestanding, elasticized flaps. An absorbent structure and liner are disposed between the elasticized flaps. To retard liquid movement away from the absorbent structure, the liner is wrapped around the side edges and partly beneath the absorbent structure. Further, an inwardly-directed face of each flap has a first Wicking Value while the liner has a second Wicking Value that is at least 2 times greater than the first Wicking Value on a gram per gram basis.

14 Claims, 3 Drawing Sheets

U.S. PATENT DOCUMENTS

| Number | Date | Name | Ref |
|---|---|---|---|
| 2,545,674 | 3/1951 | Ralph . | |
| 2,662,526 | 12/1953 | Sanford . | |
| 2,893,393 | 7/1959 | Pressley . | |
| 3,098,484 | 7/1963 | Younger . | |
| 3,364,931 | 1/1968 | Hirsch | 128/290 |
| 3,368,563 | 2/1968 | Scheier . | |
| 3,386,442 | 6/1968 | Sabee . | |
| 3,452,753 | 7/1969 | Sanford . | |
| 3,612,055 | 10/1971 | Mesek et al. . | |
| 3,658,063 | 4/1972 | Schaar . | |
| 3,807,402 | 4/1974 | Miller et al. . | |
| 3,825,006 | 7/1974 | Ralph . | |
| 3,920,017 | 11/1975 | Karami . | |
| 3,929,134 | 12/1975 | Karami . | |
| 4,041,950 | 8/1977 | Jones, Sr. . | |
| 4,090,515 | 5/1978 | Karami . | |
| 4,210,143 | 7/1980 | De Jonckheere . | |
| 4,246,900 | 1/1981 | Schroder . | |
| 4,388,075 | 6/1983 | Mesek et al. . | |
| 4,397,644 | 8/1983 | Matthews et al. . | |
| 4,397,645 | 8/1983 | Buell . | |
| 4,425,128 | 1/1984 | Motomura . | |
| 4,490,148 | 12/1984 | Beckestrom . | |
| 4,496,359 | 1/1985 | Pigneul . | |
| 4,501,587 | 2/1985 | Enloe . | |
| 4,579,556 | 4/1986 | McFarland . | |
| 4,601,717 | 7/1986 | Blevins . | |
| 4,610,681 | 9/1986 | Strohbeen et al. . | |
| 4,639,949 | 2/1987 | Ales et al. . | |
| 4,646,362 | 3/1987 | Heran et al. . | |
| 4,655,760 | 4/1987 | Morman et al. . | |
| 4,657,539 | 4/1987 | Hasse . | |
| 4,690,681 | 9/1987 | Haunschild et al. . | |
| 4,704,115 | 11/1987 | Buell . | |
| 4,704,116 | 11/1987 | Enloe . | |
| 4,710,187 | 12/1987 | Boland et al. . | |
| 4,743,246 | 5/1988 | Lawson . | |
| 4,747,846 | 5/1988 | Boland et al. . | |
| 4,753,646 | 6/1988 | Enloe . | |
| 4,795,454 | 1/1989 | Dragoo . | |
| 4,798,603 | 1/1989 | Meyer et al. . | |
| 4,816,025 | 3/1989 | Foreman . | |
| 4,834,740 | 5/1989 | Suzuki et al. . | |
| 4,846,823 | 7/1989 | Enloe . | |
| 4,846,825 | 7/1989 | Enloe et al. . | |
| 4,850,990 | 6/1989 | Huntoon et al. . | |
| 4,861,652 | 8/1989 | Lippert et al. . | |
| 4,892,528 | 1/1990 | Suzuki et al. . | |
| 4,895,568 | 1/1990 | Enloe . | |
| 4,900,317 | 2/1990 | Buell . | |
| 4,904,251 | 2/1990 | Igaue et al. . | |
| 4,909,803 | 3/1990 | Aziz et al. . | |
| 4,916,005 | 4/1990 | Lippert et al. . | |
| 4,938,753 | 7/1990 | Van Gompel et al. . | |
| 4,938,754 | 7/1990 | Mesek . | |
| 4,938,755 | 7/1990 | Foreman . | |
| 4,938,757 | 7/1990 | Van Gompel et al. . | |
| 4,940,464 | 7/1990 | Van Gompel et al. . | |
| 4,988,344 | 1/1991 | Reising et al. . | |
| 5,026,364 | 6/1991 | Robertson . | |
| 5,032,120 | 7/1991 | Freeland et al. . | |
| 5,080,658 | 1/1992 | Igaue et al. . | |
| 5,085,654 | 2/1992 | Buell . | |
| 5,114,420 | 5/1992 | Igaue et al. . | |
| 5,246,432 | 9/1993 | Suzuki et al. . | |
| 5,246,433 | 9/1993 | Hasset et al. . | |
| 5,292,316 | 3/1994 | Suzuki . | |
| 5,405,342 | 4/1995 | Roessler et al. | 604/394 |
| 5,458,591 | 10/1995 | Roessler et al. | 604/394 |
| 5,476,457 | 12/1995 | Roessler et al. | 604/394 |
| B1 3,860,003 | 4/1989 | Buell . | |

METHOD OF MANUFACTURE OF LIQUID RETAINING ABSORBENT GARMENT

This is a divisional application of application U.S. Ser. No. 08/171,578, filed on Dec. 22, 1993 now U.S. Pat. No. 5,476,458.

BACKGROUND OF THE INVENTION

The present invention relates to articles for absorbing body fluids. More particularly, the invention pertains to an absorbent garment having improved liquid containment. The invention also pertains to methods of making such absorbent garments.

Toilet training represents a transition from diapers to underpants. The use of training pants is beneficial during the training process because training pants are three-dimensional articles like underpants, but yet they also include absorbent structures to accommodate accidental voids.

Although including an absorbent structure, current training pants have still been subject to failures in the form of leakage. Such leakage commonly occurs around the leg openings of the pant. Therefore, what is lacking and needed in the art is an improved training pant that resists leakage around the leg openings.

SUMMARY OF THE INVENTION

In response to the discussed deficiencies in the prior art, a new disposable absorbent garment has been developed. Absorbent garments in one embodiment of the present invention have longitudinal and transverse axes and include a three-dimensional pant body. The pant body defines a waist opening, two leg openings and a crotch region. A containment trough, formed of a liquid impermeable material, has a base portion bonded to the crotch region and integral retaining walls transversely outward from the base portion. Each retaining wall is freestanding from the pant body. Elastic members are operatively joined to the retaining walls to define freestanding elasticized flaps. Each flap has an inwardly-directed face with a first Wicking Value. An absorbent structure is disposed between the flaps and has upper and lower surfaces, longitudinally spaced end edges, and side edges extending between the end edges. A liner is bonded to the containment trough and formed of a liquid permeable material with a second Wicking Value. The liner covers the upper surface of the absorbent structure, is wrapped over the side edges of the absorbent structure, and desirably also covers at least part of the lower surface of the absorbent structure. The second Wicking Value is at least 2 times greater than the first Wicking Value on a gram per gram basis.

This embodiment of the invention provides an absorbent garment that resists leakage around the leg openings. The containment trough, here having an integral base portion and retaining walls, is positioned beneath and transversely outward from the absorbent structure and forms the freestanding elasticized flaps. The integral containment trough has no seams between the elasticized flaps and the base portion. The integral containment trough permits absorbent garments of the invention to be produced by relatively uncomplicated manufacturing processes with fewer materials and adhesives than existing garments.

Additionally, liquid containment is enhanced in this embodiment due to the liner being wrapped around the side edges and partly beneath the absorbent structure. Rather than migrate onto the inwardly-directed faces of the flaps, liquid tends to migrate within the liner past the side edges and toward the lower surface of the absorbent structure. Liquid tends to follow the liner because of its higher Wicking Value, which is a measure of the ability of a material to transport liquid in the plane of a material.

In another aspect of the invention, the absorbent structure has a width of less than about 150 millimeters and is located within about 10 millimeters of each elasticized flap. Additionally, the flaps have a height of from about 27 to about 75 millimeters. The close proximity of the elasticized flaps to the relatively narrow absorbent structure facilitates the flaps remaining upstanding when the pant body is pulled on, while the flap height enables the flaps to remain positioned in contact with the wearer between the thigh and perineum even after a void. Wrapping the liner under the absorbent structure and forming the inwardly-directed faces of the flaps with a low wicking material are believed to retard lateral liquid movement in garments having the described relatively narrow crotch and proximately-positioned elasticized flaps.

In a further aspect of the invention, the pant body is formed of gas permeable materials and includes a center panel and at least two side panels bonded to the center panel. The base portion of the containment trough is bonded to the center panel of the pant body. The garment may also include a pair of support members formed of a gas permeable material. In one particular embodiment, each support member has an inner portion bonded to one of the retaining walls of the containment trough and an outer portion bonded to the pant body. A portion of each side panel is sandwiched between the center panel of the pant body and the outer portion of a support panel.

The support members of this aspect of the invention enable the pant body to be constructed of separate center and side panels while maintaining the overall integrity of the garment. The bond between the center and side panels is strengthened, and the overall integrity of the garment improved, by sandwiching a portion of each side panel between the center panel of the pant body and the outer portion of a support panel. Further, the support members cover the outer faces of the retaining walls and strengthen the retaining walls of the containment trough. By forming both the pant body and the support members of gas permeable materials, all portions of the garment transversely outward from the flaps are gas permeable. The resulting air circulation enhances skin wellness.

In another aspect, the absorbent structure may be completely wrapped in the liner, and the liner releasably bonded to the base portion of the containment trough. This structure allows the liner and absorbent structure to be completely removed from the pant body, either for separate disposal or replacement with a new liner/absorbent assembly.

Another aspect of the invention pertains to a method of making an absorbent garment. This method includes: supplying an outer cover having opposite longitudinally spaced front and back ends with a crotch region therebetween; supplying a containment trough formed of a liquid impermeable material, the containment trough having a base portion and integral retaining walls; bonding the base portion of the containment trough to the crotch region so that the retaining walls are positioned transversely outward from the base portion and freestanding from the outer cover; operatively joining elastic members to the retaining walls to define freestanding elasticized flaps, each flap having an inwardly-directed face with a first Wicking Value; supplying an absorbent structure having upper and lower surfaces, longitudinally spaced end edges, and side edges extending between the end edges; covering the upper surface, side edges and at least part of the lower surface of the absorbent structure with a liner formed of a liquid permeable material with a second Wicking Value, the second Wicking Value being at least 2 times greater than the first Wicking Value on a gram per gram basis; disposing the absorbent structure between the flaps; and bonding the liner to the base portion.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
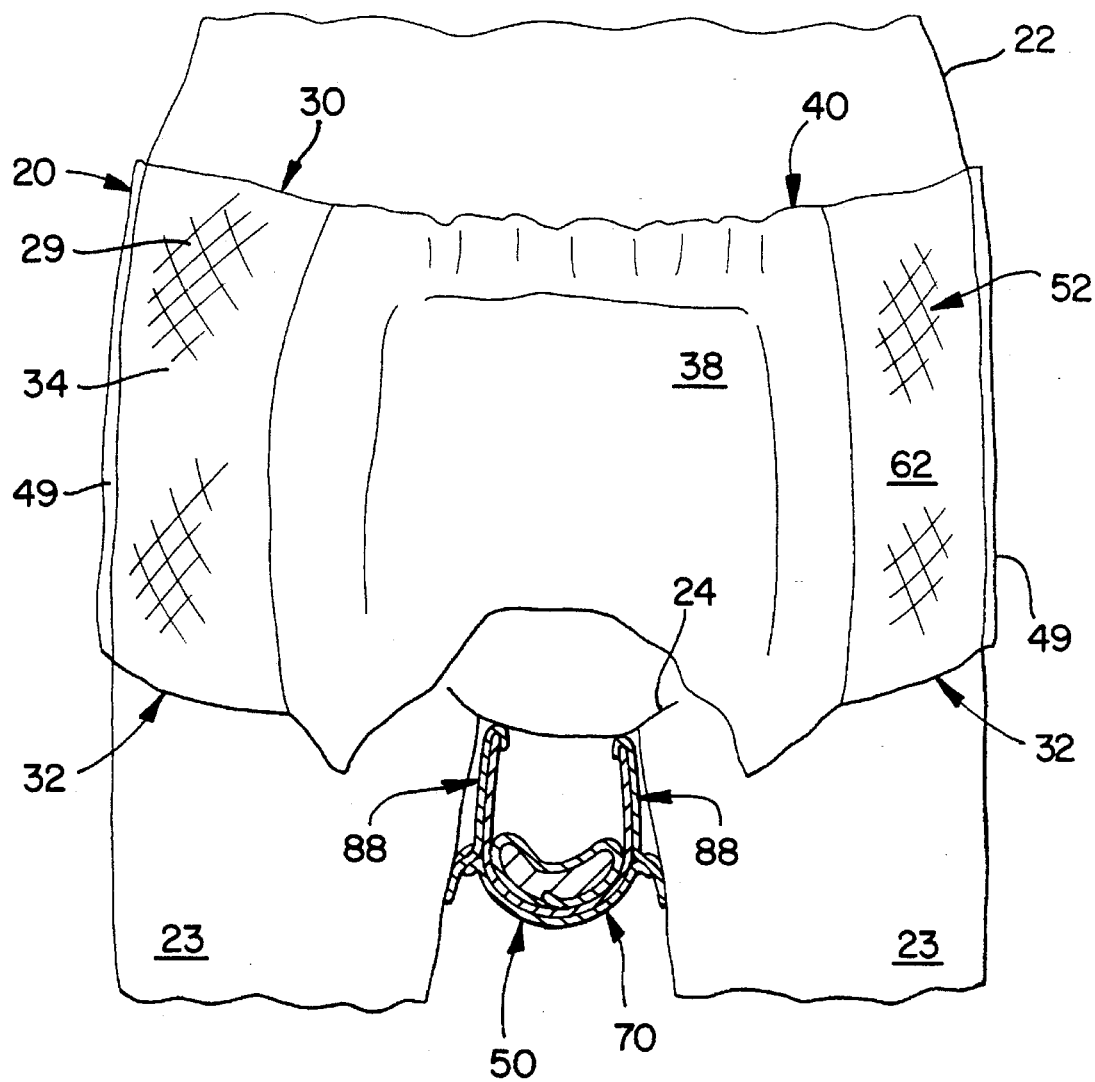
FIG. 1 is an elevational view of a disposable absorbent garment according to the present invention fitted on a child, with portions broken away for purposes of illustration.

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed," "disposed on," "disposed with," "disposed at," "disposed near," and variations thereof are intended to mean that one element can be integral with another element, or that one element can be a separate structure joined to or connected to or placed with or placed near another element.

(d) "elastic," "elasticized" and "elasticity" include that property of a material by virtue of which it tends to recover its original size and shape after removal of a force causing the deformation.

(e) "force" includes a physical influence exerted by one body on another which produces acceleration of bodies that are free to move and deformation of bodies that are not free to move. Force is expressed in grams per unit area.

(f) "freestanding" refers to a particular portion of a first element, that portion itself not being bonded to a second element so that the portion is capable of moving relative to second element.

(g) "front" and "back" are used to designate relationships relative to the garment itself, rather than to suggest any position the garment assumes when it is positioned on a wearer.

(h) "integral" is used to refer to various portions of a single unitary element rather than separate structures joined to or connected to or placed with or placed near one another.

(i) "member" when used in the singular can have the dual meaning of a single element or a plurality of elements.

(j) "operatively joined", with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(k) "outward" refers to a position relative to the center of an absorbent garment, and particularly transversely and/or longitudinally away from the longitudinal and transverse center of the absorbent garment.

(l) "permanently bonded" refers to the joining, adhering, connecting, attaching, or the like, of two elements of an absorbent garment such that the elements tend to be and remain bonded during normal use conditions of the absorbent garment.

(m) "releasably attached," "releasably bonded" and variations thereof refer to two elements being connected or connectable such that the elements tend to remain connected absent a separation force applied to one or both of the elements, and the elements being capable of separation without substantial permanent deformation or rupture. The required separation force is typically beyond that encountered during normal use of the absorbent garment.

(n) "rupture" includes the breaking or tearing apart of a material; in tensile testing, rupture refers to the total separation of a material into two parts either all at once or in stages, or the development of a hole in some materials.

(o) "stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

(p) "stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

(q) "three dimensional" refers to a garment similar to underwear, shorts or pants in that it has continuous leg and waist openings that are bounded by material of which the garment is made. The garment may or may not have manually tearable seams.

(r) "two dimensional" refers to a garment that can be opened and laid in a flat condition without destructively tearing any structure. These garments, such as diapers, do not have continuous leg and waist openings, and require a fastening device, such as adhesive tapes or hook-and-loop fasteners, to attach the garment about the wearer.

These terms may be defined with additional language in the remaining portion of the specification.

DETAILED DESCRIPTION OF THE PREFERRED EMBODIMENTS

Figure 2:
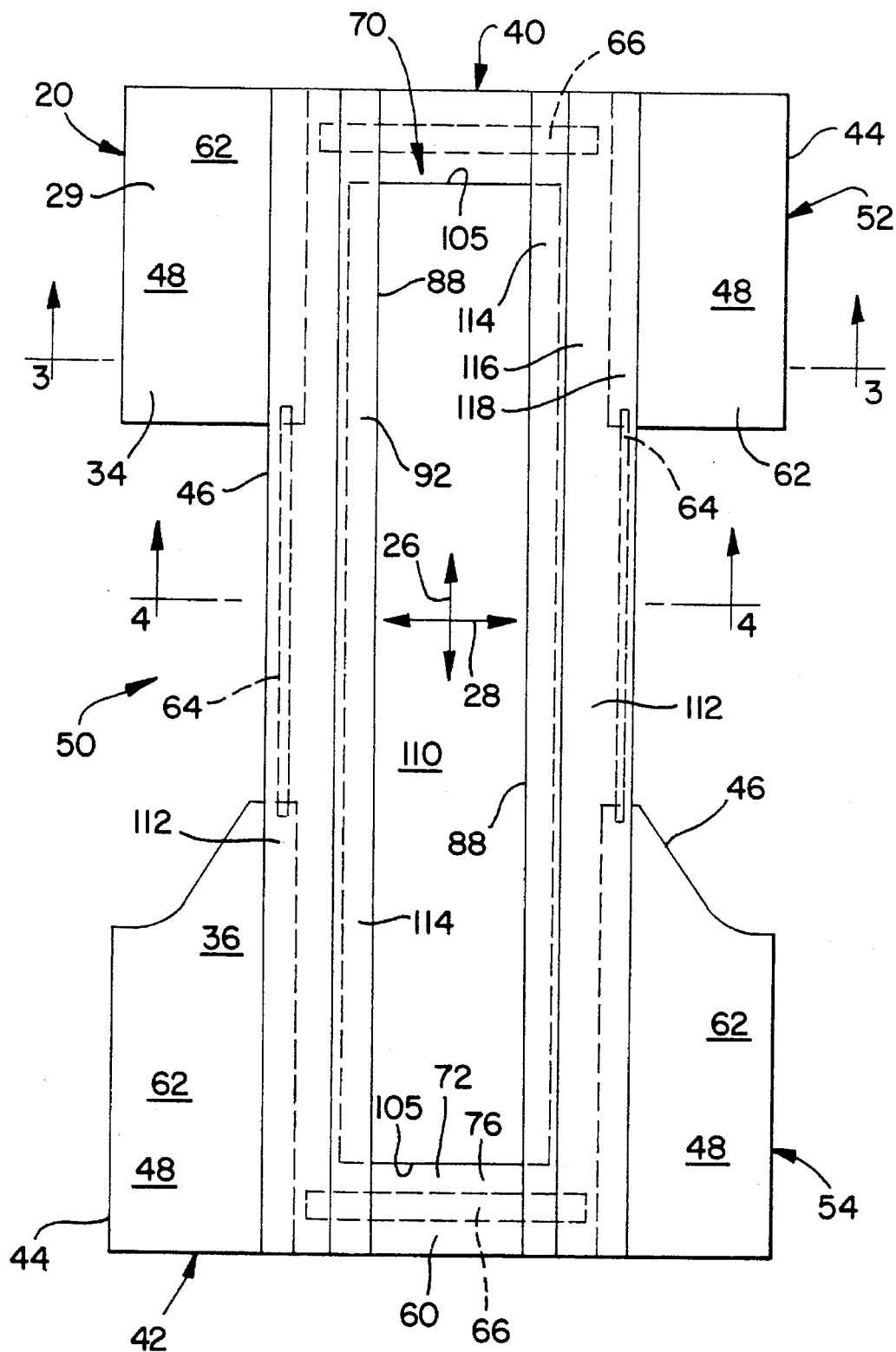
FIG. 2 is a top plan view of the disposable absorbent garment shown in FIG. 1, at an intermediate stage of assembly and in a flat and stretched condition.

With reference to FIGS. 1–2, a disposable absorbent garment 20 formed according to the present invention is shown for purposes of illustration as a three-dimensional toilet training pant for a child. The invention may also be embodied in other types of absorbent garments, such as diapers and adult incontinence products.

The training pant 20 is positioned on the torso 22 of a child in FIG. 1, where the torso includes legs 23 and a crotch 24. In FIG. 2, the training pant 20 is shown at an intermediate stage of assembly and in a flat and stretched condition. The training pant 20, which has longitudinal and transverse axes 26 and 28 that lie in the plane of the garment, includes a pant body 29. The pant body 29 is, in the finished product, three-dimensional and thus defines a waist opening 30 and two leg openings 32 (FIG. 1), through which the torso is positioned.

The pant body 29 is constructed from an outer cover 34 having opposite inner and outer surfaces 36 and 38. The outer cover 34 defines opposite longitudinally spaced front and back ends 40 and 42 and opposite side edges 44 extending between the ends. Each side edge 44 is desirably shaped to form a recessed area 46 with ear portions 48 on either end of the recessed area (FIG. 2).

The pant body 29 is assembled from the intermediate stage shown in FIG. 2 by permanently bonding the ear portions 48 of each side edge 44 together. This is illustrated in FIG. 1 by non-refastenable seams 49. The seams 49, which may be manually tearable, may be formed by any suitable means such as ultrasonic sealing, adhesive bonding, heat sealing, adhesive coated tapes, or the like. One suitable method for forming such seams is disclosed in U.S. Pat. No. 4,938,753 issued Jul. 3, 1990, to Van Gompel et al., which is incorporated herein by reference.

The assembled pant body 29 (FIG. 1) defines a crotch region 50 generally located between the leg opening 32. The crotch region 50 comprises that portion of the pant body 29 which, when worn, is positioned between the legs of the wearer and covers the lower torso of the wearer. A front waist region 52 of the pant body 29 extends generally from the crotch region 50 to the front end 40 of the outer cover 34. Similarly, a back waist region 54 extends from the crotch region 50 to the back end 42 of the outer cover 34. In general, the longitudinal extent of the waist regions 52 and 54 is related to the distance between the ends 40 and 42 of the outer cover 34 and the recessed areas 46, measured along the side edges 44.

Figure 3:
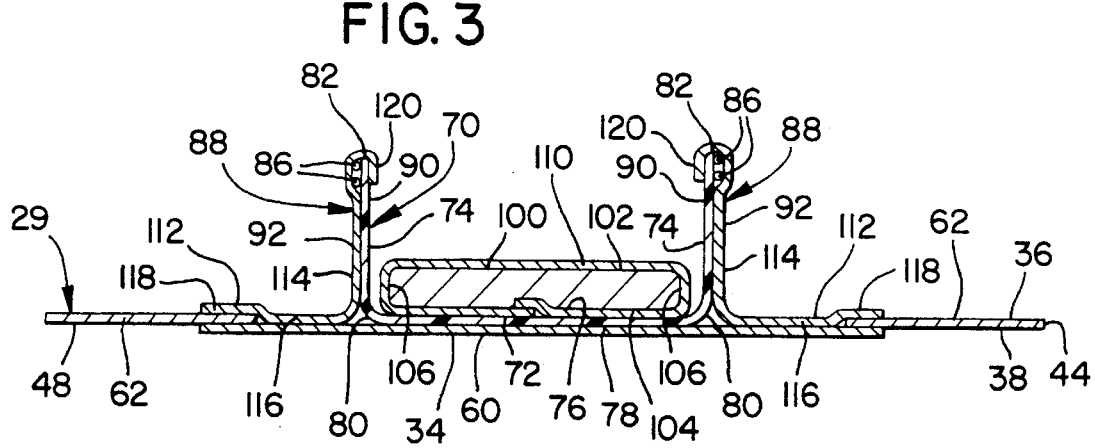
FIG. 3 is a transverse section view taken generally from the plane of the line 3—3 in FIG. 2, but with the disposable absorbent garment in an unstretched condition.
Figure 4:
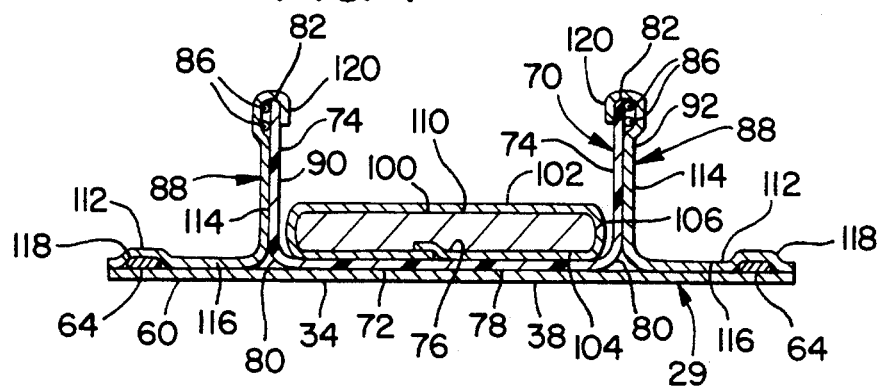
FIG. 4 is a transverse section view taken generally from the plane of the line 4—4 in FIG. 2, but with the disposable absorbent garment in an unstretched condition.

With particular reference to FIGS. 2–4, the illustrated outer cover 34 comprises a center panel 60 and four side panels 62. Each side panel 62 is positioned transversely outward from the center panel 60 and bonded thereto using adhesives, thermal bonds, ultrasonic bonds or other suitable means. The side panels 62 form the ear portions 48 of the pant body 29. Alternately, the outer cover 34 could be an integral structure having the desired recessed side shape or other shape (not shown).

The center and side panels 60 and 62 of the outer cover 34 are desirably formed of gas permeable materials, referred to as breathable materials. Further, at least the side panels 62 are also desirably formed of an elastic material capable of stretching in a direction parallel to the transverse axis 28 of the training pant 20. The outer cover panels 60 and 62 may, for instance, comprise a single layer of apertured film, a woven material, a nonwoven material or another suitable liquid permeable or liquid impermeable material. The outer cover panels 60 and 62 may also comprise a laminate material, such as a stretch bonded laminate formed of a prestretched elastic meltblown inner layer sandwiched between and attached to a pair of spunbond polypropylene nonwoven webs having a basis weight of about 13.6 grams per square meter. Suitable elastic materials can be purchased from the Shell Chemical Company of Houston, Tex., under the tradename Kraton.

In one embodiment, the side panels 62 are formed of a laminated material comprising a prestretched elastic meltblown inner layer having a basis weight of about 18 grams per square meter sandwiched between and stretch bonded to a pair of spunbond webs each having a basis weight of about 14.9 grams per square meter. The spunbond webs comprise bicomponent fibers formed of about 50 weight percent polypropylene and about 50 weight percent polyethylene in a side-by-side configuration. Alternately, suitable elastic strands may be substituted for the elastic meltblown layer.

The pant body 29 also includes leg elastic members 64 and waist elastic members 66 that are bonded to the outer cover 34 to enhance fit and performance. In particular, the leg elastic members 64 (FIGS. 2 and 4) are operatively joined to the outer cover 34 along each side edge 44 through the crotch region 50. Also, the waist elastic members 66 are operatively joined to the outer cover 34 along the front and back ends 40 and 42 (FIG. 2). The elastic members 64 and 66 may be bonded to the inner surface 36 or alternately the outer surface 38 of the outer cover 34 using adhesives, thermal bonds, ultrasonic bonds, stitching, or other suitable means. The elastic members 64 and 66 may be stretch bonded to the outer cover 34, bonded in a relaxed state to a gathered portion of the outer cover, or a combination of the two. One suitable method for attaching the elastic members 64 and 66 is disclosed in U.S. Pat. No. 4,639,949 issued Feb. 7, 1987, to Ales et al., which is incorporated herein by reference.

A containment trough 70 of the training pant 20 is formed of a liquid impermeable material and attached to the pant body 29. Suitable liquid impermeable materials may comprise a thin, substantially liquid impermeable web, adhesive coating, or sheet of plastic film such as polyethylene, polypropylene, polyvinyl chloride or similar material, and be either gas permeable or gas impermeable. Alternately, the containment trough 70 may comprise a nonwoven, fibrous web which has been suitable constructed and/or treated to be substantially liquid impermeable, or a layered or laminated material, such as a thermally bonded plastic film and nonwoven web composite.

The containment trough 70 has a base portion 72, retaining walls 74 integral with the base portion, and first and second major planar surfaces 76 and 78. The base portion 72 is oriented along the longitudinal axis 26 of the training pant 20 such that the retaining walls 74 are positioned transversely outward from the base portion. The base portion 72 is bonded on the second surface 78 to the center panel 60 of the outer cover 34 in at least the crotch region 50. More desirably, the base portion 72 extends the full length of the center panel 60 between the front and back ends 40 and 42 and is bonded thereto over its full length (FIG. 2). As such, the base portion 72 covers the waist elastic members 66 and sandwiches them between the containment trough 70 and the center panel 60 of the outer cover 34.

The retaining walls 74 represent the lateral portions of the containment trough 70 that are not directly bonded to the pant body 29. Rather, the retaining walls 74 are integral with the base portion 72 which is bonded to the outer cover 34 of the pant body 29. As a result, the retaining walls 54 are freestanding from the pant body. With particular reference to FIGS. 3 and 4, each retaining wall 74 has an inner border 80 adjacent the base portion 72 and a distal edge 82 remote from the base portion.

Elastic members 86 are operatively joined to each retaining wall 74 adjacent the distal edge 82. The elastic members 86 may be stretch bonded or otherwise attached to the retaining wall 74 on either the first surface 76 or second surface 78. The elastic members 86 may comprise a dry-spun coalesced filament elastomeric thread sold under the trade name LYCRA and available from E. I. Du Pont de Nemours and Company. Alternately, the elastic members 86 may be formed of a stretch bonded laminate including at least one nonwoven gatherable layer and an elastic layer, or other typical elastics utilized in making disposable absorbent garments.

The elastic members 86 and retaining walls 74 together define freestanding elasticized flaps 88 of the training pant 20. It is intended, however, as described hereinafter, that the elasticized flaps 88 may comprise additional components besides the retaining walls 74 and the elastic members 88. The flaps 88 desirably have a height in the crotch region 50 of from about 25 to about 75 millimeters, and particularly from about 30 to about 50 millimeters. Flap height is generally the maximum distance a distal edge of a flap 88 in the finished pant 20 can be positioned from the pant body 29. In the illustrated embodiment, the flap height is the maximum distance between the inner boarder 80 of the retaining wall 74 and the distal edge of the flap 88, which here is approximately equal to the distance between the inner boarder 80 and the distal edge 82 of the retaining wall 74.

Each flap has an inwardly-directed face 90 and an opposite outwardly-directed face 92. As shown in FIGS. 3 and 4, the inwardly-directed face 90 is directed toward the transverse center of the training pant 20 when the flap 88 is upstanding from the pant body 29. The inwardly-directed face 90 may comprise the first surface 76 of the containment trough 70 as illustrated, or comprise in whole or in part another material positioned on the first surface of the containment trough (for example zone 120 discussed hereinafter).

An absorbent structure 100 (FIGS. 3 and 4) of the training pant 20 is disposed between the flaps 88 to receive liquid waste from the wearer. The absorbent structure 100 has upper and lower surfaces 102 and 104, longitudinally spaced end edges 105 (FIG. 2), and side edges 106 extending between the end edges. The absorbent structure may be T-shaped, I-shaped, rectangular or irregularly-shaped. Desirably, however, the width of the absorbent structure 100 measured between the side edges 106 is from about 40 to about 150 millimeters, and particularly the width is less than about 125 millimeters, such as from about 75 to about 100 millimeters, in the crotch region 50. Further, the base portion 72 of the containment trough 70 desirably has a width measured parallel to the transverse axis 28 of the training pant 20 which is approximately the same as the width of the absorbent structure 100. Desirably, the widths of the absorbent structure 100 and base portion 72 are selected such that at some location between the front and back ends 40 and 42 the absorbent structure is located within about 20 millimeters of each flap 88, and particularly within about 10 millimeters of each flap 88, and more desirably such that the flaps 88 indirectly (due to liner 110) contact the side edges 106 of the absorbent structure 100.

A liner 110 formed of a liquid permeable material covers the upper surface 102 of the absorbent structure 100 and is bonded to the containment trough 70. The liner 110 is desirably wrapped over the side edges 106 and thereafter extends to a position between the lower surface 104 of the absorbent structure 100 and the base portion 72 of the containment trough 70. Specifically, the liner 110 desirably covers the upper surface 102, is wrapped over and covers the side edges 106, and is wrapped under and covers at least part of the lower surface 104 of the absorbent structure 100. As illustrated in FIGS. 3 and 4, the liner 110 may completely wrap the absorbent structure 100. The liner 110 may be bonded to itself and bonded to the base portion 72 beneath the absorbent structure 100.

Particularly in absorbent garments having relatively narrow absorbent structures 100 in the crotch region 50, it is important to retard movement of liquid transversely outward from the absorbent. Accordingly, the liner 110 of the training pant 20 is desirably wrapped beneath the absorbent structure 100 to promote liquid movement toward the lower surface 104 of the absorbent structure, rather than movement transversely outward over the inwardly-directed faces 90 of the flaps 88.

The liner material 110 and the material forming the inwardly-directed faces 90 of the flaps 88 are selected to retard the lateral movement of liquid. Specifically, the material for the liner 110 is selected to the promote liquid transport within the plane of the liner so that liquid remains in contact with the absorbent structure 100 and tends to travel toward the lower surface 104 of the absorbent structure. Also, the material forming the inwardly-directed faces 90 of the flaps 88 is selected to have poor liquid transport capabilities relative to the liner 110. The material forming the inwardly-directed faces 90 of the flaps 88 may consist only of the containment trough material, may consist of a laminate having a distinct material bonded to the retaining walls 74, or comprise a combination of the containment trough material at one location on the inwardly-directed faces 90 and another distinct material bonded to the retaining walls 74 at another location on the inwardly-directed faces 90 (see zone 120 discussed hereinafter). In particular, the liner 110 desirably has a Wicking Value at least 2 times greater, and more desirably at least 3 times greater, for example at least 3.5 times greater, than that of the inwardly-directed surface 90 of the flaps 88, on a gram per gram basis as discussed below. This is particularly beneficial in absorbent garments where the width of the absorbent structure 100 in the crotch region 50 is not more than about 100 millimeters.

The procedure for determining the Wicking Value of a material is as follows. The procedure employs an acrylic board measuring 225 by 125 by 6 millimeters, with a clamps at one end to hold a sample of the material; a tray; a mechanism for suspending the acrylic board above the tray;

a timer; and a saline solution, particularly saline distributed by Baxter Healthcare Corp. of McGraw Park, Ill., under the tradename Certified Blood Bank Saline Cat. No. B83158-1. The material to be tested is cut into 5 samples each measuring 130 by 400 millimeters. For each sample, the sample weight in grams is determined and recorded. The sample is then folded over the non-clamp end of the acrylic board and the longitudinal ends of the sample secured by the clamps. The weight of the combined acrylic board and sample is determined and recorded as the initial combined weight. The combined acrylic board and sample is suspended above the tray containing the saline solution. The combined acrylic board and sample is lowered until the non-clamp end of the acrylic board is level with surface of the saline, causing the portion of the sample folded over the non-clamp end to be contacting the saline. The combined acrylic board and sample is removed after 15 seconds and weighted (recording weight optional). The combined acrylic board and sample is then again suspended and lowered until the non-clamp end of the acrylic board is level with surface of the saline. The combined acrylic board and sample is removed after 6 minutes, weighed, and the weight recorded as the final combined weight. The Wicking Value for an individual sample on a gram per gram basis is the final combined weight minus the initial combined weight, and the result divided by the sample weight. The Wicking Value on a gram per gram basis for the material is the average of the 5 individual sample values.

As noted above, the inwardly-directed faces 90 of the flaps 88 may include at one location only the containment trough material and at another location another distinct material bonded to the containment trough material (see zone 120). In such circumstances, the Wicking Value of the inwardly-directed faces 90 is the lowest Wicking Value of the containment trough material measured alone, the combination distinct material and containment trough material measured together, and the distinct material measured alone.

In one particular embodiment, the liner 110 is formed of a spunbond polypropylene nonwoven web having a basis weight of 24 grams per square meter and including a hydrophilizing surfactant treatment, such as is available from Rohm and Haas Corporation of Philadelphia, Pa., under the tradename Triton. Further, the first surface 76 of the containment trough retaining walls 74 form the inwardly-directed faces 90 of the flaps 88. The containment trough 70 is formed of 0.015 millimeter thick polyethylene film. The liner 110 has a Wicking Value of about 0.66 gram per gram, and the inwardly-directed faces 90 of the flaps 88 have a Wicking Value of about 0.19 gram per gram. Materials for use as a liner 110 may be treated with surfactant in order to make non-wettable polymeric fibers of the liner Wettable. Even when such a surfactant coating washes away, however, fluid will be directed toward the lower surface 104 of the absorbent structure 100 due to the liner 110 being wrapped under the lower surface 104. The inwardly-directed faces 90 of the flaps may also be treated, such as with silicone, oils, waxes or the like, to reduce their wicking ability.

The training pant 20 also includes a pair of support members 112 (FIGS. 2-4) which enhance the structural integrity of the pant and facilitate bonding of the elastic members 64, 66 and 86. Each support member 112 is desirably formed of a gas permeable material, for example a spunbonded, meltblown or bonded-carded web composed of synthetic polymer filaments, such as polypropylene, polyethylene, polyesters or the like. Each support member 112 has an inner segment 114, a middle segment 116, and an outer segment 118. The support members 112 are positioned so that the segments 114, 116 and 118 extend parallel to the longitudinal axis 26 of the training pant 20, and the inner segments 114 are located nearer the transverse center of the pant.

With reference to FIGS. 3 and 4, the inner segments 114 are freestanding from the pant body 29 but positioned against and bonded to the retaining walls 74 on their second surfaces 78. The inner segments 114 thus form an additional part of the elasticized flaps 88. The middle segments 116 of the support members 112 are desirably bonded directly to the inner surface 36 of the outer cover 34. In the crotch region 50, the outer segments 118 are bonded to the inner surface 36 of the outer cover 34 such that the leg elastic members 64 are sandwiched therebetween (FIG. 4). In the front and back waist regions 52 and 54, however, a portion of each side panel 62 is sandwiched between and bonded to the center panel 60 of the outer cover 34 and an outer segment 118 of a support member 112 (FIG. 3).

Desirably, each inner segment 114 of the support members 112 has an inner zone 120 (FIGS. 3 and 4) remote from the middle and outer segments 116 and 118 that is folded over onto and bonded to the first surface 76 of the containment trough 70 along the distal edges 82. The folded over inner zone 120 provides additional structural support to the flaps 88. They also cover the distal edges 82 of the containment trough 70 which could be uncomfortable against the skin.

The training pant 20 may be constructed by separately forming the pant body 29 with the side panels 62 bonded to the center panel 60. The leg and waist elastic members 64 and 66 are adhesively attached to the outer cover 34 with a suitable adhesive, such as are available from Findley Adhesives, Inc., Wauwatosa, Wis. The adhesives can be applied in any manner such as spraying, slot-coating extrusion, printing, or the like. The adhesive can be sprayed in any desired configuration or design such as continuous or discontinuous beads or swirls, a melt-blown pattern, spray pattern, or the like. Additional description of the construction of this type of training pant is disclosed in U.S. Pat. No. 4,940,464 issued Jul. 10, 1990 to Van Gompel et al., assigned to the assignee of this application and incorporated herein by reference. A description of a training pant with an integral pant body is described in U.S. patent application Ser. No. 07/809,993, by Van Gompel et al., filed Dec. 18, 1991, which is assigned to the assignee of this application and incorporated herein by reference.

The middle and outer segments 116 and 118 of the support members 112 may then be bonded to the center panel 60 and side panels 62. The outer segments 118 of the support members 112 sandwich the leg elastic members 64 between the outer segments 118 and the center panel 60 of the outer cover 34 in the crotch region 50 and sandwich portions of each side panel 62 between the outer segments 118 and the center panel 60 in the front and back waist regions 52 and 54.

The containment trough 70 is then attached to the pant body 29. In particular, the base portion 72 is bonded to the center panel 60, and the freestanding retaining walls 74 are bonded to the freestanding inner segments 114 of the support members 112 with the elastic members 86 therebetween. The inner zone 120 may be folded over the distal edge 82 of the containment trough 70 and bonded to the first surface 76.

The absorbent structures 100 may be separately formed and desirably completely wrapped by the liner 110. The absorbent structure 100 and liner 110 may be secured together by adhesives, thermal bonds or other suitable means. The liner 110 is then bonded, with either a releasable or permanent bond, to the center panel 60 of the outer cover 34 immediately between the elasticized flaps 88.

Assembly of the training pant 20 is completed by bonding the ear portions 48 of each side edge 44 together with suitable seams 49. The training pant 20 is then ready to be worn as suggested by FIG. 1. In use, the training pant 20 resists leakage around the leg openings 32 due in part to the integral containment trough 70 being positioned both beneath and transversely outward from the absorbent structure 100. The freestanding elasticized flaps 88 are formed in part by the retaining walls 74 of the containment trough 70. Thus, the integral trough 70 has no seams between the elasticized flaps 88 and the base portion 72.

The integral containment trough 70 allows a reduction in the amount of liquid impermeable materials needed in construction of the pant 20, as well as fewer adhesives. The integral base portion 72 and retaining walls 74 of the containment trough 70 also allow consistent assembly of a liquid impermeable trough without "gaps" or "holes" due to machine placement variations. Further, in embodiments where the pant body 29 and the support members 112 are formed of gas permeable materials, all portions of the garment 20 transversely outward from the flaps 88 are gas permeable, which improves air circulation in the pant.

Absorption of liquid applied to the liner 110 into the absorbent structure 100 is aided by the liner being wrapped around the side edges 106 and partly beneath the lower surface 104 of the absorbent structure 100. Additionally, liquid more readily wicks within the liner 110 adjacent the absorbent structure 100 rather than migrate along the inwardly-directed faces 90 of the flaps 88, due to the difference in the Wicking Values of the liner 110 and the inwardly-directed faces 90 of the flaps 88.

Figure 5:
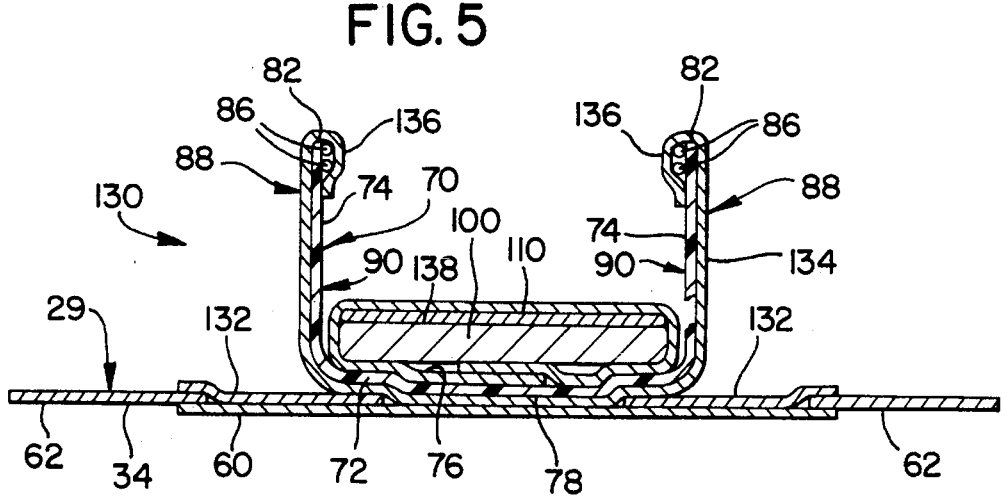
FIG. 5 is a transverse section view similar to FIG. 3, but illustrating an alternate disposable absorbent garment according to the present invention.

An alternate training pant 130 according to the present invention is illustrated in part in the section view of FIG. 5, where components similar to those previously described have been given the same reference numeral. The training pant 130 includes a pant body 29 formed of an outer cover 34 that can have center and side panels 60 and 62. The training pant 130 also includes first support members 132 bonded to the center panel 60 and sandwiching part of the side panels 62 between the first support member and the center panel. Rather than two separate first support members 132 as shown in FIG. 5, the pant 130 could include a single first support member covering for instance the entire center panel 60 (not shown).

A containment trough 70 having first and second surfaces 76 and 78 is disposed on and indirectly bonded to the pant body 29. A second support member 134 is disposed on the second surface 78 of the containment trough 70. In particular, the second support member 134 is disposed on the base portion 72 and positioned partially between the second surface 78 and the center panel 60 of the outer cover 34. Also, the second support member 134 is disposed on each retaining wall 74, against the second surface 78. The second support member 134 includes zones 136 along its longitudinal side edges which are folded over the distal edges 82 of the containment trough 70 and bonded to the first surface 76 of the containment trough. Elastic members 86 which in part form the elasticized flaps 88 may be sandwiched between the second support member 134 and either the first or second surface 76 or 78 of the retaining walls 74.

The first and second support members 132 and 134 enhance the integrity of the training pant 130 in the same manner as the support members 112 described in relation to FIGS. 1–4. The first and second support members 132 and 134 may be formed of the same material as support members 112 described previously. As mentioned above, the absorbent structure 100 may be completely wrapped in the liner 110 and permanently or releasably bonded to the pant body 29. The absorbent structure 100 may also include an additional layer 138 to assist in the acquisition and/or distribution of liquid. The liner 110 and absorbent structure when releasably bonded to the pant body 29 may be removed from the pant, either for separate disposal or replacement.

A wide variety of materials may be used to construct the aforementioned components of the absorbent articles 20 and 130. Numerous examples of materials used in constructing absorbent articles are described in the aforementioned U.S. patents and application incorporated by reference herein.

The liner 110 may be any soft, flexible, porous sheet which passes fluids therethrough and desirably forms the stated wicking relationship relative to the inwardly-directed faces 90 of the flaps 88. The liner 110 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The liner 110 has a pore size that readily allows the passage therethrough of liquids, such as urine and other body exudates. The liner 110 may be selectively embossed or perforated with discrete slits or holes extending therethrough, such as an apertured film material.

The absorbent structure 100 is desirably an air-formed batt of cellulosic fibers (i.e., wood pulp fluff). One preferred type of wood pulp fluff, which is available under the trade designation CR1654 from Kimberly-Clark Corporation of Neenah, Wis., U.S.A., is a bleached, highly absorbent sulphate wood pulp containing softwood fibers. Optionally, the absorbent structure 100 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent structure 100 may also include compounds to increase its absorbency, such as an effective amount of organic or inorganic high-absorbency materials. For example, the absorbent structure 100 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst Celanese Corporation, and Allied Colloids, Inc. Typically, the high-absorbency material is capable of absorbing at least about 15 times its weight in water, and preferably is capable of absorbing more than about 25 times its weight in water.

The high-absorbency material can be distributed or otherwise incorporated into the absorbent structure 100 employing various techniques. For example, the high-absorbency material can be substantially uniformly distributed among the fibers comprising the absorbent structure. The materials can also be nonuniformly distributed within the absorbent structure fibers to form a generally continuous gradient with either an increasing or decreasing concentration of high-absorbency material, as determined by observing the concentration moving inward from the base portion 72 of the containment trough 70. Alternatively, the high-absorbency material can comprise a discrete layer separate from the fibrous material of the absorbent structure 100, or can comprise a discrete layer integral with the absorbent structure.

The absorbent structure 100 may also include a tissue wrap layer to help maintain the integrity of the fibrous core. This tissue wrap typically comprises a hydrophilic cellulosic material, such as creped wadding or a high wet-strength tissue. The absorbent structure 100 may further include an additional layer 138 (FIG. 5) for managing, transporting, accommodating, permitting, or directing rapid and/or sudden flow of urine therethrough and into contact with the absorbent materials. The additional layer desirably functions to draw liquid from the bodyside surface of the liner 110 and then permit desorption by the absorbent materials. Suitable materials are disclosed in U.S. Pat. No. 4,798,603 issued Jan. 17, 1989, to Meyer et al. and European Patent Application EP 0 539 703 A1, published May 5, 1993, to Hanson et al. which patent and application are incorporated herein by reference.

The leg and waist elastic members 64 and 66 may be formed of a stretch bonded laminate. In particular, the stretch bonded laminate may comprise at least one nonwoven gatherable layer and an elastic layer. Alternatively, the leg and waist elastic members 64 and 66 may be formed of a dry-spun coalesced filament elastomeric thread sold under the trade name LYCRA and available from E. I. Du Pont de Nemours and Company. Still alternatively, the elastic members may be formed of other typical elastics utilized in making disposable absorbent garments, such as a thin ribbon of elastic material as disclosed in U.S. Pat. No. 4,940,464 issued Jul. 10, 1990, to Van Gompel et al., which is incorporated herein by reference. Elasticity could also be imparted by extruding a hot melt elastomeric adhesive to the outer cover 34. Other suitable elastic gathering means are disclosed in U.S. Pat. Nos. 4,938,754 to Mesek and 4,388,075 to Mesek et al.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Also, while the invention has been described with respect to use for training pants, certain of its advantages and features are adaptable for use in other absorbent garments. Therefore, the invention should not be limited by the specific embodiments described, but only by the claims.

We claim:

1. A method of making an absorbent garment, comprising the steps of:

supplying an outer cover having opposite longitudinally spaced front and back ends with a crotch region therebetween;

supplying a containment trough having a liquid impermeable base portion and integral liquid impermeable retaining walls;

bonding the base portion of the containment trough to the crotch region so that the retaining walls are positioned transversely outward from the base portion and freestanding from the outer cover;

operatively joining elastic members to the retaining walls to define freestanding elasticized flaps, each flap comprising one of the liquid impermeable retaining walls and having an inwardly-directed face that is adapted to transport liquid in the plane of the inwardly-directed face as defined by a first Wicking Value greater than zero;

supplying an absorbent structure having upper and lower surfaces, longitudinally spaced end edges, and side edges extending between the end edges;

covering the upper surface, side edges and at least part of the lower surface of the absorbent structure with a liner formed of a liquid permeable material that is adapted to transport liquid in the plane of the liquid permeable material as defined by a second Wicking Value, the second Wicking Value being at least 2 times greater than the first Wicking Value on a gram per gram basis;

disposing the absorbent structure between the flaps; and bonding the liner to the base portion.

2. The method of claim 1, wherein the outer cover is formed of a gas permeable material, and the absorbent garment transversely outward from the flaps is gas permeable.

3. The method of claim 1, wherein the first Wicking Value is less than about 0.25 gram per gram and the second Wicking Value is more than about 0.5 gram per gram.

4. The method of claim 1, wherein the absorbent structure has a width of less than about 150 millimeters and is located within about 10 millimeters of each flap.

5. The method of claim 4, wherein each flap has a height of from about 25 to about 75 millimeters.

6. The method of claim 1, wherein the step of covering the absorbent structure comprises completely wrapping the absorbent structure in the liner.

7. The method of claim 6, wherein the step of bonding the liner to the base portion comprises releasably bonding the liner to the base portion.

8. The method of claim 1, wherein the outer cover comprises a center panel and side panels.

9. The method of claim 8, further comprising:

providing a pair of support members, each support member having an inner segment and an outer segment;

bonding the inner segments to the retaining walls; and bonding the outer segments to the outer cover.

10. The method of claim 9, wherein the outer cover and support members are each formed of a gas permeable material, and the absorbent garment transversely outward from the flaps is gas permeable.

11. A method of making absorbent garment having longitudinal and transverse axes, comprising the steps of:

supplying a three-dimensional pant body defining a waist opening, two leg openings, and a crotch region;

supplying a containment trough having a liquid impermeable base portion and integral liquid impermeable retaining walls;

bonding the base portion to the pant body so that the retaining walls are positioned transversely outward from the base portion and freestanding from the pant body;

operatively joining elastic members to the retaining walls to define freestanding elasticized flaps, each flap comprising one of the liquid impermeable retaining walls and having an inwardly-directed face that is adapted to transport liquid in the plane of the inwardly-directed face as defined by a first Wicking Value greater than zero, each flap having a height of from about 25 to about 75 millimeters;

supplying an absorbent structure having a width of less than about 150 millimeters;

wrapping the absorbent structure in a liner formed of a liquid permeable material that is adapted to transport liquid in the plane of the liquid permeable material as defined by a second Wicking Value, the second Wicking Value being at least 2 times greater than the first Wicking Value on a gram per gram basis;

disposing the absorbent structure between the flaps; and bonding the liner to the base portion.

12. The method of claim 11, wherein the pant body is formed of a gas permeable material, and the absorbent garment transversely outward from the flaps is gas permeable.

13. The method of claim 11, wherein the first Wicking Value is less than about 0.2 gram per gram and the second Wicking Value is more than about 0.6 gram per gram.

14. The method of claim 11, wherein the step of bonding the liner to the base portion comprises releasably bonding the liner to the base portion.

* * * * *